(12) United States Patent
Blaustein et al.

(10) Patent No.: US 6,350,265 B1
(45) Date of Patent: Feb. 26, 2002

(54) COVER FOR PLATE FOR MANDIBULAR OSTEOSYNTHESIS

(75) Inventors: David I. Blaustein, Chicago, IL (US); Brian S. Schumacher, Jacksonville, FL (US)

(73) Assignee: Walter Lorenz Surgical, Inc., Jacksonville, FL (US)

( * ) Notice: Subject to any disclaimer, the term of this patent is extended or adjusted under 35 U.S.C. 154(b) by 0 days.

(21) Appl. No.: 09/482,997

(22) Filed: Jan. 13, 2000

(51) Int. Cl.[7] ................................................ A61B 17/56

(52) U.S. Cl. .......................................... 606/71; 606/72

(58) Field of Search ............................. 606/69, 70, 71, 606/72, 73, 104; 128/846, 848, 857

(56) References Cited

U.S. PATENT DOCUMENTS

| | | | | | |
|---|---|---|---|---|---|
| 2,443,363 A | * | 6/1948 | Townsend | ..................... | 606/71 |
| 3,659,595 A | * | 5/1972 | Haboush | ...................... | 606/71 |
| 4,484,570 A | * | 11/1984 | Sutter | .......................... | 606/72 |
| 4,903,691 A | * | 2/1990 | Heinl | .......................... | 606/70 |

* cited by examiner

Primary Examiner—Michael A. Brown
(74) Attorney, Agent, or Firm—Harness, Dickey & Pierce, P.L.C.

(57) ABSTRACT

An apparatus for osteosynthesis of a mandible. An elongated plate has a plurality of apertures. A cover has a lateral wall, a top wall, and a medial wall defining a channel. A portion of the mandible is resected to leave a bony gap. The elongated plate is received within the channel of the cover, and the cover is received within the bony gap to alleviate growth of soft tissue against the elongated plate. Screw fasteners received through the apertures of the elongated plate secure the plate to the mandible.

5 Claims, 4 Drawing Sheets

COVER FOR PLATE FOR MANDIBULAR OSTEOSYNTHESIS

BACKGROUND OF THE INVENTION

1. Field of the Invention

The present invention relates to surgical repair of fractures, deformities, diseases and surgical osteotomies of bone. More particularly, the present invention relates to a method and apparatus for mandibular osteosynthesis in which a portion of the mandible is resected to make way for subsequent bone grafting.

2. Discussion of the Related Art

In various craniofacial surgical procedures, it is necessary to align and secure two bone portions in a relatively fixed relationship to each other. As examples, the need to establish such a secured relationship can arise from a fracture of the bone or from an oncology resection of the bone. To ensure that the bone can regenerate in the proper orientation and fuse the fracture, or maintain mandibular shape after an oncology resection, it is important that the bone portions be fixed in the desired position.

It is known in the art to provide metal plates for the repair of bone fractures. Such plates generally are secured to bone portions with fasteners, especially screws. Among other applications, such plates and fasteners are used to provide rigid stabilization of craniofacial fractures and oncology resections. The plates conventionally employed for cranial and facial osteosynthesis generally comprise small, generally flat, elongated sections of metal. The plate sections contain round and perhaps elongated screw holes at various points along their lengths for receiving screws to fasten the plate sections to bone.

Because no surface of the human skeleton is completely flat, existing plates must be extensively twisted, formed and bent during surgery to conform to portions of the skeleton on which they are to be affixed. Significant time is expended during surgery shaping and re-shaping metal plates to conform adequately to bone surfaces. This expenditure of time increases anesthesia requirements and operating room time and also increases the potential for infection.

In one commonly used technique for mandibular reconstruction, an initially flat plate is bent to conform to the contours of the surface of the mandible. The conformed plate is secured to the mandible by a plurality of screw fasteners received through holes in the plate. The screw fasteners penetrate into and gain purchase in the bone. Subsequently, the fasteners and plate are removed to allow surgical access to the mandible, e.g., to remove a cancerous growth, leaving a gap in the mandible. Finally, the plate is fastened again to the mandible by engaging the fasteners with the previously formed holes in the mandible. The bone gap in the mandible is left alone. After a wait of an appropriate time, e.g., 6–24 months, to make sure that the cancer has not returned, a bone graft is placed in the gap. During the months of waiting in which the gap is open, soft tissue grows into the gap and rubs against the plate, causing soft tissue irritation, or dehiscence.

While known systems utilizing plates and fasteners for cranial and facial osteosynthesis have proven to be acceptable for certain applications, such systems are nevertheless susceptible to improvements that may enhance their performance. Known systems do not provide plates having enhanced screw placement options together with enhanced bending ease at desired locations, while preserving the integrity of screw holes at bending sites and avoiding interference between screws in adjacent screw holes. Known systems also do not provide a way to prevent the ingrowth of soft tissue into the gap in the mandible left by resection of cancerous bone. These and other desirable improvements are provided by the present invention, preferred embodiments of which are described below with reference to the drawings.

SUMMARY OF THE PRESENT INVENTION

According to one aspect of the present invention, an apparatus for osteosynthesis of a mandible includes an elongated plate having a plurality of apertures and a cover having a lateral wall, a top wall, and a medial wall defining a channel. The elongated plate is received within the channel of the cover.

According to another aspect of the present invention, a method of surgically repairing a mandible includes the steps of providing an elongated plate having a plurality of apertures, and providing a fastener having means for engaging the mandible and having means for engaging an aperture of the plate. The elongated plate is secured to the mandible with the fastener. A cover is provided having a lateral wall, a top wall, and a medial wall defining a channel. A portion of the mandible is resected leaving a bony gap. The elongated plate is received within the channel, and the cover is received within the bony gap.

It is an object of the present invention to provide an osteosynthesis plate for use in surgical repair of a mandible and to alleviate growth of soft tissue into a gap in the mandible left by surgical resection of the mandibular bone and to alleviate dehiscence of such soft tissue by protecting the plate from contact by such soft tissue.

It is a further object of the present invention to alleviate growth of soft tissue into a gap in the mandible left by surgical resection of the mandibular bone.

Additional objects and advantages of the present invention will be apparent from the descriptions below of preferred embodiments and their methods of use, made with reference to the drawings.

DETAILED DESCRIPTION OF THE PRESENT INVENTION

The following description of the preferred embodiments of the present invention is merely exemplary in nature and is in no way intended to limit the invention or its application or uses.

Figure 1:
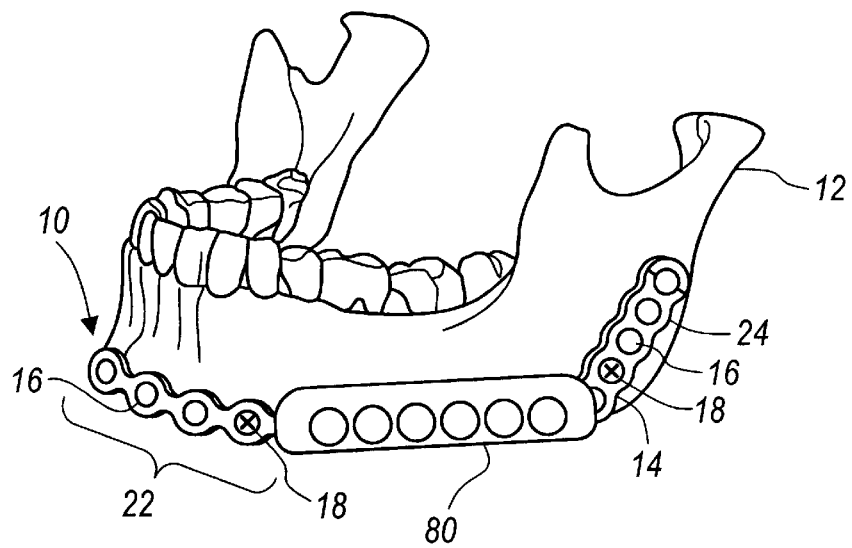
FIG. 1 is a perspective view of a mandibular osteosynthesis system configured in accordance with the present invention, illustrated in operative association with a human mandible and particularly showing a locking plate and screw fasteners, and further showing a plate cover in operative association with the locking plate, according to the teachings of the present invention.

Referring to FIG. 1, a system constructed in accordance with a preferred embodiment of the present invention is generally identified by reference numeral 10. The system 10 is shown operatively associated with a human mandible 12. However, it will become apparent to those skilled in the art that certain aspects of the present invention have applicability to other bones of the skeleton and other surgical procedures.

Figure 2:
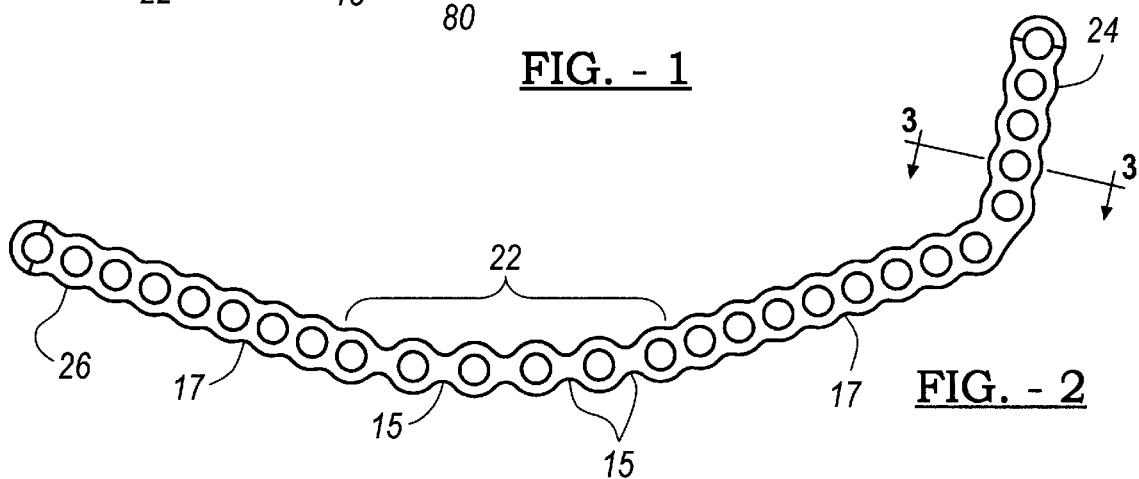
FIG. 2 is an illustration of the locking plate shown in FIG. 1 according to the teachings of the present invention.
Figure 3:
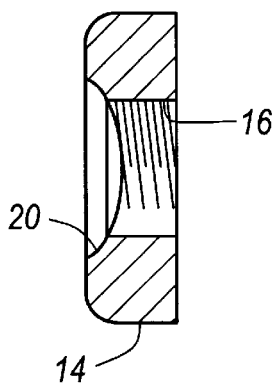
FIG. 3 is a cross-sectional view taken along the line 3—3 of FIG. 2.
Figure 4:
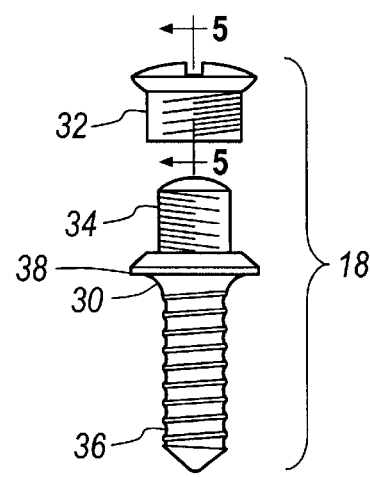
FIG. 4 is an exploded view of one of the fasteners shown in FIG. 1 according to the teachings of the preferred embodiment of the present invention.

With continued reference to FIG. 1 and with reference to FIGS. 2, 3 and 4, the system 10 of the present invention is shown to include an elongated plate 14 and a plurality of fasteners 18. The plate 14 is formed to include a plurality of apertures 16, each adapted to receive a fastener 18 for interconnecting the plate 14 with the mandible 12. Each aperture 16 preferably includes an oval countersink 20 and is internally threaded. As described further below, the internal threading of apertures 16 permits locking of fastener 18 to plate 14. For this reason, plate 14 is also referred to herein as a locking plate 14.

The locking plate 14 is shown to include generally a central portion 22, and first and second ends 24 and 26. The first end 24 is precontoured to conform generally to the shape of the posterior portion of the mandible 12 near the temporal mandibular joint. The central portion 22 and the second end 26 also are precontoured such that plate 14 can be bent around the anterior portion, or symphysis, of mandible 12 and lie adjacent the side of mandible 12 opposite to that side of mandible 12 to which first end 24 lies adjacent. The central portion 22 of plate 14, after bending, lies adjacent the symphysis. Prior to bending, second end 26 may be regarded as curving superiorly in a sagittal plane relative to central portion 22.

At the first and second ends 24 and 26, respectively, and in next adjacent regions of plate 14, the plurality of apertures 16 of plate 14 are disposed in relatively close spaced relationship. In contrast, in the central portion 22 of plate 14, intended to be bent intraoperatively to lie adjacent to the symphysis, the plurality of apertures 16 are disposed in relatively widely spaced relationship. In the central portion 22, regions 15 of plate 14 that are disposed between next adjacent apertures 16, are narrower in width than are regions 17 of plate 14 that are disposed between next adjacent apertures located outside central portion 22. The narrower, or necked, regions 15, in combination with the wider spacing of the nearby apertures 16, make plate 14 more easily bendable in central portion 22. More particularly, plate 14 is more susceptible to being bent, and being bent to a greater degree, between holes in the central portion 22 than outside the central portion 22. This arrangement facilitates bending of plate 14 in the region of the symphysis, where the natural contour of the bone dictates that the plate 14 be bent more severely than in other regions to conform to the contour of the bone.

In one application, the locking plate 14 is constructed of titanium. More preferably, the locking plate 14 is constructed of commercially pure, Grade 2 or Grade 4 titanium. However, it will be appreciated by those skilled in the art that other materials having suitable performance and biocompatibility characteristics may be employed. Preferably, the locking plate 14 is inelastically deformable so as to retain its shape once contoured to conform to the shape of the mandible 12.

Figure 5:
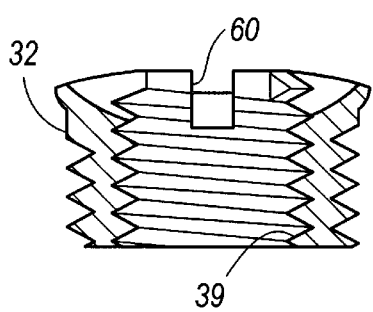
FIG. 5 is a cross-sectional view taken along the line 5—5 of FIG. 4.
Figure 6:
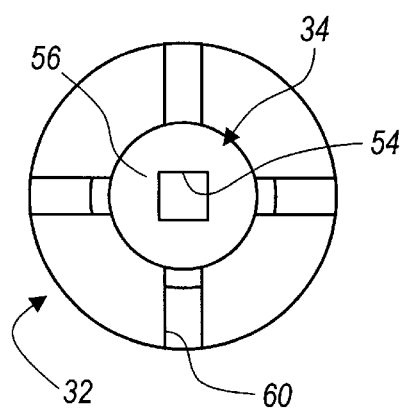
FIG. 6 illustrates an end view of the head of the fastener shown in FIG. 4 according to the present invention.

With reference to FIGS. 4–6, the fastener 18 of the present invention is shown to generally include a main body 30 and a head member 32. The main body 30 includes an upper shaft portion 34 and a lower shaft portion 36. The lower shaft portion 36 is externally threaded and adapted to penetrate and engage the mandible or bone 12 in a conventional manner. Insertion of the lower shaft portion into the bone is limited by a flange 38 interposed between the upper and lower shaft portions 34 and 36. The upper shaft portion 34 is externally threaded and adapted to engage an internally threaded aperture 39 of the head member 32. The head member 32 is externally threaded for engaging one of the plurality of internally threaded apertures 16 of the locking plate 14.

In one application, the thread pitches of the upper shaft portion 34, lower shaft portion 36 and the external threads of the head member 32 are common. The external threads of the head member 32 and the externally threaded lower shaft portion 36 have a common thread lead. In the exemplary embodiment illustrated, the externally threaded lower shaft portion 36 has a single lead configuration while the external threads of the upper shaft portion 34 and head member 32 have a double lead configuration.

In use, a malleable template (not shown) is positioned on the mandible 12 and bent to the general shape of the adjacent bone surface. Next, the locking plate 14 is bent to approximately the shape of the template and positioned on the mandible 12 so that certain apertures 16 may be selectively used as a guide for drilling holes (not specifically shown) in the mandible 12 for receiving the fasteners 18. The bending is generally more severe around the symphysis, or chin area. It is desirable to bend the plate between the apertures to maintain the integrity of the internal threads of the apertures. A first one of the fasteners 18 is passed through a selected one of the apertures 16 and rotated so that the externally threaded lower portion 36 engages and is driven into the hole in the mandible 12. For example, the first end 24 of the locking plate 14 may be secured first to the mandible 12 with a first fastener 18. As the externally threaded lower portion 36 of the fastener 18 is driven into the bone 12, the external threads of the head member 32 eventually engage the internally threaded aperture 16 of the locking plate 14 and advance simultaneously with the external threads of lower portion 36. This is possible as a result of the common thread lead shared between the lower portion 36 and the head member 32.

Additional fasteners 18 are used to interconnect the locking plate 14 with the bone 12 in a substantially identical manner. As shown in FIG. 1, four fasteners are used to interconnect the locking plate 14 with the bone 12. However, it will be appreciated by those skilled in the art that any number of fasteners 18 may be employed depending on a particular application. As each fastener is engaged with the bone 12, the locking plate 14, previously having been bent to conform to the shape of the mandible, is drawn into its operative position adjacent to the bone 12.

At this point of the surgical procedure, the head members 32 of each of the threaded fasteners 18 are unthreaded from their respective upper portions 34. This allows the surgeon to remove the locking plate 14 from the fasteners 18 and displace the locking plate 14 from the bone. This provides access to the bone 12 for accomplishing a desired surgical procedure, e.g., removal of a cancerous growth. The lower portions 36 of fasteners 18 remain embedded in the bone. When the locking plate 14 is removed, it retains its shape due to its inelastic deformation. When the surgical procedure is complete, the locking plate 14 is replaced by inserting the upper portions 34 of the fasteners 18 through the respective apertures 16 and simultaneously engaging the internal threads of the head members 32 with the external threads of the upper portion 34, and the external threads of the head member 32 with the internal threads of the aperture 16. Since the fasteners 18 are not removed from the bone 12 after initial insertion, fastener-to-bone purchase is not compromised.

Referring now to FIGS. 1 and 13–16, a cover 80 for use in association with locking plate 14 is illustrated. Cover 80, as preferred, is constructed of medical grade polyethylene such as ultra high molecular weight polyethylene or high molecular weight polyethylene. Other biocompatible materials, including metals such as titanium or stainless steel, may be used to construct cover 80. FIG. 1 shows cover 80 in place affixed to locking plate 14 and serving to partially fill a gap left in the mandibular bone 12 by surgical resection of cancerous bone. Cover 80 protects locking plate 14 in the vicinity of the bony gap from growth of soft tissue adjacent plate 14. Such soft tissue growth, as would ordinarily occur during a waiting period following resection of the cancerous bone, if permitted to occur adjacent locking plate 14, would result in tissue irritation, or dehiscence. Cover 80 is placed upon locking plate 14 and secured thereto prior to locking plate 14 being replaced onto the fasteners 18 that have been secured to bone. Cover 80 is so placed upon locking plate 14 as to be received within the resected bony gap.

More specifically, cover 80 comprises a generally U-shaped sleeve having a lateral wall 82, a medial wall 84, and a top wall 86 defining a channel 88 having a lateral surface 90, a medial surface 92, and a top surface 94. Cover 80 includes a first longitudinal end 96, a second longitudinal end 98, and a bottom surface 100. Channel 88 is open at bottom surface 100 and at each longitudinal end 96 and 98. Channel 88 has a width defined by the spacing between lateral surface 90 and medial surface 92, which width is slightly larger than the thickness of locking plate 14, as shown in FIG. 3. Channel 88 has a depth defined by the spacing between top surface 94 and bottom surface 100, which depth is slightly larger than the width of locking plate 14, as shown in FIG. 3. Consequently, cover 80 fits over locking plate 14 such that locking plate 14 is received within channel 88 in close fitting arrangement. Cover 80 also includes a plurality of round apertures 102 having a countersunk bevel 104 at lateral wall 82. Apertures 102 are through-holes in lateral wall 82 and communicate between channel 88 and lateral wall 82. Apertures 102 are spaced longitudinally along cover 80 at a pitch that corresponds to the spacing pitch of apertures 16 of locking plate 14. Thus, when cover 80 is fitted over locking plate 14, apertures 102 can be aligned with apertures 16.

To secure cover 80 in place on locking plate 14, a plurality of small, self-tapping screws 104 are provided. Screws 104 are inserted through apertures 102 from the lateral side of cover 80 and through the aligned apertures 16 of locking plate 14, and are screwed into the polyethylene of medial wall 84 in a self tapping manner. The heads 106 of screws 104 are of sufficiently small diameter to pass freely through apertures 102 and be received freely within apertures 16 of locking plate 14. Screw heads 106 do not intimately engage apertures 16, but instead reside freely therein merely to prevent displacement of cover 80 relative to locking plate 14 in the superior-inferior, and anterior-posterior directions. It is appreciated that fastening means other than screws 104 could be used to secure cover 80 to locking plate 14, including the provision of a snap-fit between structural features of cover 80 and locking plate 14.

After an appropriate waiting period to ensure that the cancer has not recurred, screws 104 can be removed and cover 80 can be removed from locking plate 14 to permit a bone graft to be implanted in the bony gap of the mandible formerly occupied by cover 80.

Cover 80 is rounded to a generally oval shape in cross-section, particularly at top walls 86 and medial wall 84, to provide a smooth surface free of sharp edges against which soft tissue can grow without risk of dehiscence.

Figure 7:
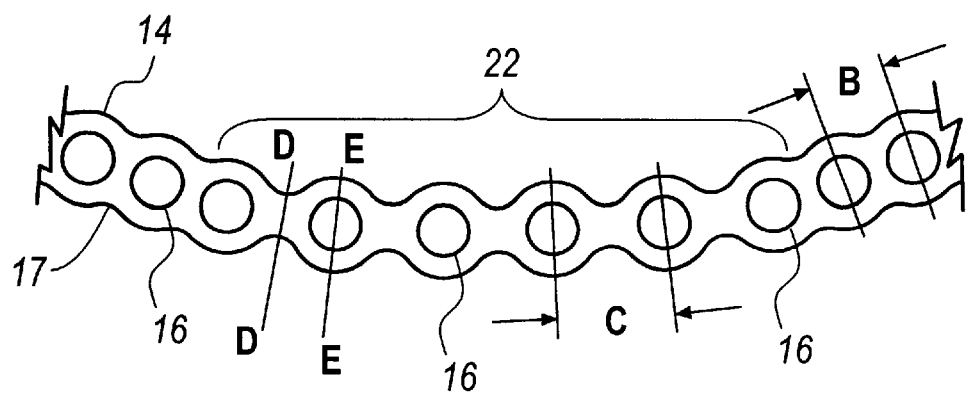
FIG. 7 is a detail illustration of the embodiment of the locking plate of FIG. 2.

With reference to FIG. 7, a detail view is shown of central portion 22 of plate 14 and next adjacent regions of plate 14 outside of central portion 22. Outside of central portion 22, the plurality of apertures 16 are evenly spaced along plate 14, having a preferred center to center spacing, B, of less than about 0.34 inches, and a most preferred center to center spacing of about 0.295 inches. The regions 17 between adjacent apertures 16 outside of central portion 22 have a preferred width in the plane of plate 14 of about 0.18 to about 0.32 inches, and a most preferred width of about 0.20 inches to about 0.24 inches. Within central portion 22, the plurality of apertures 16 also is evenly spaced along plate 14, but at a wider spacing than that of the apertures 16 outside of central portion 22. The preferred center to center spacing, C, of apertures 16 is greater than about 0.39 inches, and as most preferred, about 0.411 inches, within central portion 22. Within central portion 22, the regions 15 between adjacent apertures 16 have a preferred width in the plane of plate 14 of about 0.12 inches to about 0.22 inches, and a most preferred width of about 0.16 inches. Plate 14 has a substantially constant thickness over its entire length in the range of about 0.06 inches to about 0.12 inches, with most preferred thicknesses of about 0.079 or about 0.102 inches. Each of apertures 16 has a diameter of about 0.10 inches to about 0.18 inches, and a most preferred diameter of about 0.16 inches. As preferred, the major diameter of oval countersink 20 is about 0.211 inches, and the minor diameter of oval countersink 20 is about 0.188 inches. The cross-sectional area of plate 14 taken in a transverse plane D—D in region 15 between adjacent widely spaced apertures in central portion 22 is less than the cross-sectional area of plate 14 taken in a transverse plane E—E diametrically across an aperture 16. With a preferred plate thickness of about 0.079 inches, the preferred cross-sectional area in plane D—D is about 0.0126 square inches and the preferred total cross-sectional area in plane E—E is about 0.014 square inches. Alternatively, with a preferred plate thickness of about 0.102 inches, the preferred cross-sectional area in plane D—D is about 0.016 square inches and the preferred total cross-sectional area in plane E—E is about 0.018 square inches.

In central region 22, the increased center-to-center spacing of apertures 16, together with the reduced width of region 15 between adjacent apertures, and further in combination with the lesser cross-sectional area of plate 14 in regions 15 relative to the cross-sectional area of plate 14 through apertures 16, results in certain advantages over the prior art. More specifically, enhanced ease of bending of plate 14 is provided in central portion 22, with the bending occurring between adjacent apertures 16 with little or no distortion of the plate 14 surrounding each aperture 16. The prevention of distortion of the boundaries of apertures 16 is particularly advantageous in that the internal threading and circularity of apertures 16 is preserved, thereby ensuring that apertures 16 are able to receive fasteners 18 therethrough even after plate 14 has been bent in central portion 22 to conform to the shape of the adjacent mandible bone. The increased spacing between adjacent apertures in central portion 22 is further advantageous in that it alleviates interference between the shanks of fasteners 18 received through adjacent apertures 16 in central portion 22 in the case where central portion 22 has been bent to a relatively small radius to conform to the symphysis of the mandible.

The location of central portion 22, and the total length of central portion 22, is chosen to ensure that some part of central portion 22 will fall on the symphysis of the mandible in about 90% of adult patients. To conform to the mandible, plate 14 must be bent to a smaller radius in the vicinity of the symphysis than in the vicinity of other portions of the mandible. As preferred, the total length of central portion 22 is about 2.35 inches. Central portion 22 starts about 2.50 inches from the sharp angular transition in plate 14 near the first end 24.

Figure 8:
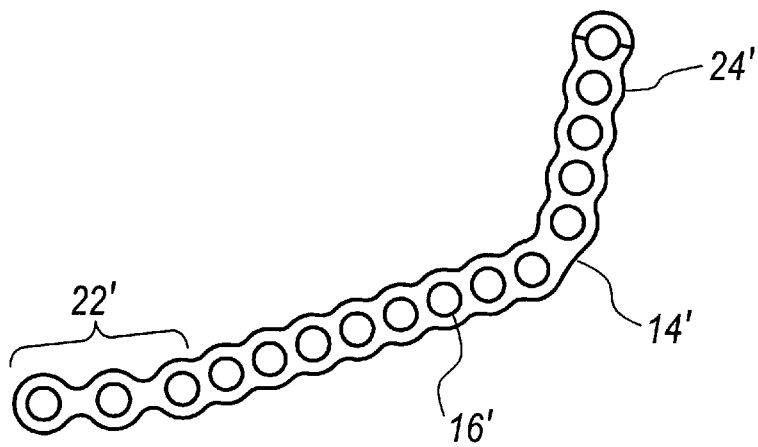
FIG. 8 is an illustration of an alternative embodiment of a locking plate configured according to the present invention.
Figure 9:
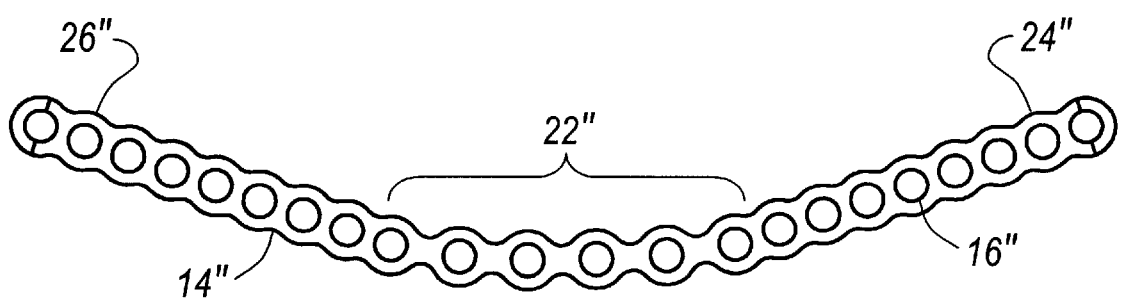
FIG. 9 is an illustration of yet another alternative embodiment of a locking plate configured according to the present invention.
Figure 16:
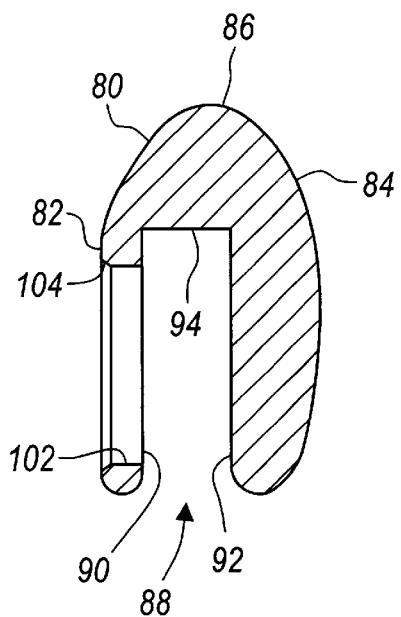
FIG. 16 is a cross-sectional view of the plate cover of FIG. 1, taken along plane 16—16 of FIG. 13 and viewed in the direction of the arrows.
Figure 14:
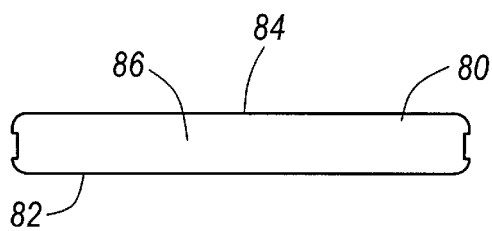
FIG. 14 is a top view of the plate cover of FIG. 1.
Figure 13:
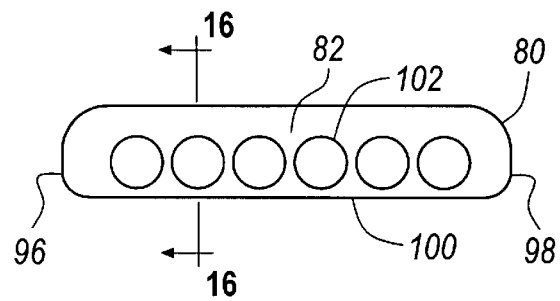
FIG. 13 is an elevation view of the plate cover of FIG. 1.
Figure 17:
FIG. 17 is an elevation view of a screw useful in combination with the plate cover of FIG. 1.
Figure 15:
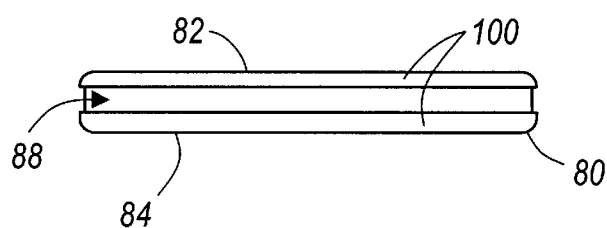
FIG. 15 is a bottom view of the plate cover of FIG. 1.

With reference to FIGS. 8 and 9, alternative embodiments are shown of a locking plate constructed in accordance with the present invention. Portions of the alternative embodiments corresponding to previously described embodiments are indicated by like primed or double primed reference numerals. In FIG. 8, plate 141 is truncated in the center of central portion 22, having no second end 26. Plate 141 is useful in surgical applications in which it is known that the locking plate 141 need not extend past the centerline of the symphysis. In FIG. 9, plate 14" is useful is surgical applications in which it is known that the locking plate need not extend superiorly toward the temporal mandibular joint. Any of plates 14, 141 and 14" can be cut to any desired length intraoperatively to accommodate the surgical procedure. Other possible embodiments (not shown) would include apertured plates generally similar to plates 14, 141 and 14", in which the plate is initially straight rather than having a preformed curve. With such straight plates, the desired curve would be formed intraoperatively.

Figure 10:
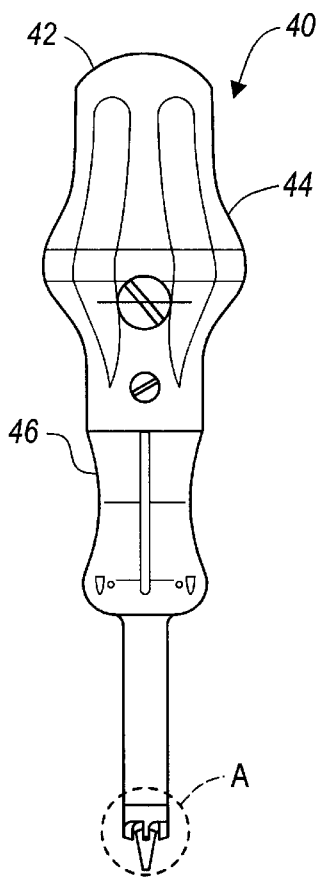
FIG. 10 is an illustration of a tool useful in connection with the mandibular osteosynthesis system of the present invention.
Figure 11:
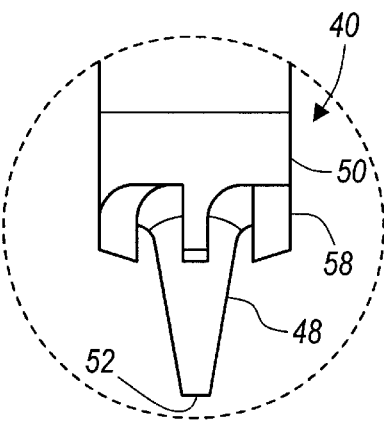
FIG. 11 is an enlarged view illustrating the detail shown in circle A identified in FIG. 10.
Figure 12:
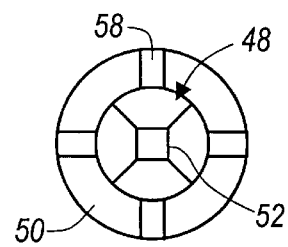
FIG. 12 is an enlarged end view of the tool shown in FIG. 14.

With reference to FIGS. 10–12, one suitable tool for use in connection with the system 10 of the present invention is shown and generally identified with reference numeral 40. The tool includes a handle 42 having an upper portion 44 and a lower portion 46. The upper and lower portions 44 and 46 are rotatable relative to one another about the longitudinal axis of the tool 40. The upper portion 44 is adapted to rotate together with a first drive portion 48, while the lower portion 46 of the handle 42 is adapted to rotate together with a second drive portion 50.

With continued reference to FIGS. 10–12, and further reference to FIGS. 5–6, the first drive portion 48 includes a generally rectangular tip 52 adapted to engage a generally rectangular aperture 54 provided in a top surface 56 of the upper shaft portion 34 of each fastener 18. The second drive portion 50 is illustrated to include four drive elements generally equally spaced about the first drive member 48. The drive elements 58 are adapted to engage a corresponding number of slots 60 equally spaced about the head member 32 of each fastener 18.

After the holes are drilled into the mandible 12, the surgeon selects a fastener with the head portion 32 threaded onto the upper shaft portion 34 of the main body 30 and engages the drive elements 58 of the tool 40 with the slots 60 of the head member 32. Simultaneously, the tip 52 of the drive member 48 engages the rectangular aperture 54 of the upper shaft portion 34. The surgeon grasps the upper and lower portions 44 and 46 of the handle 42 and rotates the tool 40 in a conventional manner. This action causes the head member 32 to threadedly engage an aperture 16 of locking plate 14 and simultaneously causes the threads of the lower shaft portion 36 of the fastener 18 to engage the hole provided in the bone 12.

Once all of the fasteners 18 are initially inserted into the bone 12, the surgeon again engages the drive elements 58 with the head 32. The thumb and forefinger are used to rotate the lower portion 46 of the handle 42 and in turn to rotate the head portion 32 of the fastener 18 in a counterclockwise direction. Simultaneously, the palm and remaining fingers grasp the upper portion 44 of the handle 42 so that the lower portion 46 can be rotated relative thereto. This action removes the head member 32 from its aperture 16. Since the main body portion 30 of the fastener 18 is not simultaneously rotated, the head portion 32 is unthreaded therefrom. In a similar manner, after the desired surgical procedure is performed on the mandible 12, the head portion 32 is returned to threaded engagement with both the aperture 16 of the plate 14 and the upper shaft portion 32 of the main body portion 30. When the locking plate 14 is operatively associated with the mandible 12 as shown in FIG. 1, the locking plate 14 is adjacent to but slightly displaced from the bone 12.

In this regard, the flange 38, which is, interposed between the upper and lower externally threaded portions 34 and 36 of the fasteners 18 limits downward translation of the removable head member 32. The thickness of the head member 32 is greater than the thickness of the locking plate 14. As a result, when a head member 32 is completely threaded on to the upper portion 34 of an associated fastener 18, the head member 32 extends beyond the locking plate 14 toward the bone and the locking plate 14 is displaced from the bone 12. Such spacing reduces resorption of the bone that otherwise might occur if the locking plate 14 were to contact the bone 12 directly.

In the preferred embodiment, the fasteners 18 are constructed from titanium 6AL4V alloy. However, it will be appreciated by those skilled in the art that other materials of having suitable strength and biocompatible characteristics may be incorporated.

The foregoing discussion discloses and describes merely exemplary embodiments of the present invention. One skilled in the art will recognize from such discussion and from the accompanying drawings and claims, that various changes, modifications and variations can be made therein without departing from the spirit and scope of the invention. For example, the configuration of the locking plate 14 shown in the drawings is one example of a locking plate suitable for use with the teachings of the present invention. Those skilled in the art will understand that various other shapes may be employed. For example, the locking plate 14 may be straight, angled, curved or any combination thereof. In certain applications, the locking plate 14 may extend about the entire mandible 12. The cover 80 may be of different lengths to fit the length of the resected gap in the mandible, as may be appropriate.

We claim:

1. An apparatus for osteosynthesis of a mandible comprising:

an elongated plate having a plurality of apertures;

a cover having a lateral wall, a top wall, and a medial wall defining a channel, said elongated plate being received within said channel, said lateral wall defining a plurality of apertures passing through said lateral wall, said medial wall positioned adjacent to said lateral wall and formed as a solid wall; and at least one screw operable to be passed through one of said apertures in said lateral wall of said cover and one of said apertures in said elongated plate to engage said solid medial wall of said cover, whereby said cover is attached to said elongated plate.

2. The apparatus of claim 1, in which said apertures of said cover and said apertures of said plate are substantially aligned.

3. The apparatus of claim 1, in which said elongated plate has a thickness, said channel of said cover has a lateral surface, a medial surface and a top surface, said channel has a width defined by the spacing between said lateral and medial surfaces, and said width of said channel is slightly greater than the thickness of said elongated plate.

4. The apparatus of claim 3, in which said elongated plate has a width, said cover has a bottom surface, said channel of said cover is open at said bottom surface and said channel has a depth defined by the spacing between said top surface of said channel and said bottom surface of said cover, and said depth of said channel is slightly greater than the width of said elongated plate.

5. A method of surgically repairing a mandible comprising the steps of:

a) providing an elongated plate having a plurality of apertures;

b) providing a first fastener having means for engaging said mandible and having means for engaging an aperture of said plate;

c) securing said elongated plate to said mandible with said first fastener;

d) providing a cover having a lateral wall, a top wall, and a medial wall defining a channel, said lateral wall having a plurality of apertures and said medial wall formed as a solid wall;

e) resecting a portion of said mandible to leave a bony gap;

f) receiving said elongated plate within said channel;

g) receiving said cover within said bony gap;

h) providing a second fastener operable to attach said cover to said elongated plate; and i) attaching said cover to said elongated plate by passing said second fastener through one of said apertures in said lateral wall of said cover and one of said apertures in said elongated plate and engaging said solid medial wall.

* * * * *